(12) United States Patent
Takeshita et al.

(10) Patent No.: US 6,468,784 B1
(45) Date of Patent: Oct. 22, 2002

(54) APPARATUS AND METHOD FOR OOCYTES OR EGGS SELECTION

(75) Inventors: Tomoko Takeshita, Higashimatsuyama (JP); Jun Otomo, Tokyo (JP); Shokichi Matsunami, Tokorozawa (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/022,734

(22) Filed: Dec. 20, 2001

(30) Foreign Application Priority Data

May 18, 2002 (JP) ........................................ 2001-149957

(51) Int. Cl.[7] ................................................ C12M 1/34
(52) U.S. Cl. ................................ 435/287.1; 435/285.2; 435/287.3; 204/403.01
(58) Field of Search ........................... 435/285.2, 287.1, 435/287.3; 204/403.01; 422/82.02

(56) References Cited

U.S. PATENT DOCUMENTS 5,541,081 A * 7/1996 Hardy et al. .................. 435/25
6,001,617 A * 12/1999 Raptis ...................... 435/173.1
6,193,647 B1 * 2/2001 Beebe et al. ................... 600/33
6,377,057 B1 * 4/2002 Borkholder ................. 324/447
2001/0005774 A1 * 6/2001 Kato et al. ................... 600/345
2001/0011154 A1 * 8/2001 Kato et al. ................... 600/345
2001/0029320 A1 * 10/2001 Trumbull et al. ........... 600/300

FOREIGN PATENT DOCUMENTS

JP  11299496 A * 11/1999

* cited by examiner

Primary Examiner—David A. Redding

(57) ABSTRACT

A method or an apparatus for selecting oocytes or eggs based on at least one objective criterion, such as membrane potential, comprises a step or means for selecting a plurality of oocytes or eggs having a certain size with a filter or the like, and a step or means for measuring a membrane potential of each of the oocytes or eggs thereby sorting out those with a membrane potential within a specified range. The selected oocytes or eggs are sold or transferred together with the measurement information or an injected sample of interest.

6 Claims, 5 Drawing Sheets

APPARATUS AND METHOD FOR OOCYTES OR EGGS SELECTION

BACKGROUND OF THE INVENTION

1. Field of the Invention

The present invention relates to an apparatus and a method for selecting oocytes or eggs. It also relates to an oocytes or egg population having a specific level of membrane potential and to a method of selling or transferring the same.

2. Description of Related Art

Oocytes have been widely used for the purpose of introducing thereinto a gene, dye, protein, peptide, drug or like sample to confirm the action, analyze the genetic function, or producing the gene product protein, for instance.

The main criterion employed in the art for selecting oocytes or eggs is the appearance. The criteria for selecting Xenopus laevis (African clawed toad) oocytes are, among others, that the diameter is 1.2 mm, that the shape is perfectly spherical, that the boundary between the black surface and white surface is distinct, and that there is no mottle or spot. The selection work is carried out manually under a microscope.

The selection of oocytes or eggs based on the appearance has the problem that the oocytes or eggs sorted out may fluctuate in quality depending on the ability and skill of each individual technician. One of the causes is that the selection criteria are rather ambiguous and discretionary. In the prior art, the oocytes or eggs sorted out can hardly be ranked. Thus, for example, the survival rate, the fertilization rate, the efficiency in introducing a sample, such as a gene, vary from cell to cell. Further, it is difficult to correct or control the fluctuations among parents in terms of survival rates, fertilization rates and gene transfer efficiency, for instance. As a result, it is only by chance that cells show no great fluctuations in survival rates, fertilization rates, and gene transfer efficiency. It is an object of the present invention to formulate certain oocyte or egg selection criteria numerically.

Furthermore, in the prior art, no due consideration has been given to the storage of data on the cells selected. Thus, it is difficult to establish correlations between data regarding selection standards and later cellular responses. Accordingly, it is another object of the invention to find such correlations.

Since, in the prior art, oocytes have been selected manually, mass production is impossible.

Accordingly, it is a further object of the present invention to produce, sell, and transport oocytes or eggs guaranteed being selected according to an established standard.

SUMMARY OF THE INVENTION

In order to accomplish the above objects, the present invention provides an apparatus and method for selecting oocytes or eggs which comprise, or comprise the use of, measuring means for selecting oocytes or eggs and selecting means for sorting the oocytes or eggs based on the measurement results.

Thus, the present invention provides a method or mechanism for selecting oocytes or eggs having a certain size out of a plurality of oocytes or eggs by means of a filter or the like as well as a step or mechanism for measuring the plurality of oocytes or eggs for membrane potential and sorting out those having a certain membrane potential from among them. In this manner, it provides oocytes or eggs uniform in quality.

The present invention first provides an apparatus for selecting oocytes or eggs which comprises measuring means for measuring the membrane potential of oocytes or eggs, and selecting means for selecting the oocytes or eggs based on the membrane potential measurement results. By this, it obtains oocytes or eggs with a certain specific level of membrane potential.

The present inventors discovered certain correlations between the membrane potential and the appearance characteristics, ex. the shape, the distinctness of the boundary between the black surface and white surface, and the presence or absence of mottles or spots, of various oocytes or eggs, especially Xenopus laevis oocytes. More specifically, they found that those oocytes, which are nearly spherical, have a distinct boundary between the black and white surfaces and are free of any mottle or spot, and have a membrane potential maintained at about −70 mV shortly after isolation. On the other hand, those cells, which are rather non-spherical, show an unclear boundary and/or have a mottle(s) or spot(s), also have a shallower membrane potential (larger negative membrane potential, hence smaller absolute potential value). By utilizing the findings and measuring the membrane potential, the invention does without the prior art appearance observation step in a selection process.

The preferred methods for measuring the membrane potential include a method based on the technique of intracellular recording or a voltage sensitive dye method. The voltage sensitive dye method comprises injecting a dye into (staining) a cell in advance, and detecting the change in the wavelength of light absorbed by the dye according to the change in the membrane potential.

The intracellular recording method comprises measuring the potential difference between the inside and outside of the cell membrane. In carrying out this method, one electrode is disposed outside the cell membrane and a second electrode inside the cell membrane, then the potential difference between them is measured. The second electrode is inserted into the cell to a depth of about 0.1 $\mu$m–0.5 mm form the cell surface.

Furthermore, the inner of the container to be used in the membrane potential measurement has a metal coating for grounding such that the measurement can be performed simply and rapidly.

The present inventors further discovered that when a gene is introduced into oocytes, the protein function expression efficiency varies depending on the membrane potential of the oocytes (before gene introduction). Thus, for preventing the protein function expression efficiency from fluctuating among oocytes, it is important to select oocytes having the same membrane potential. The present invention provides an apparatus for selecting oocytes or eggs comprising means for selectively collecting oocytes or eggs having a specific level of membrane potential. By this, it has become possible to select oocytes or eggs having a specific level of membrane potential.

Furthermore, the present invention provides an apparatus for selecting oocytes or eggs comprising measuring means for measuring the sizes of oocytes or eggs and selecting means for selecting the oocytes or eggs based on the size measurement results. By this, it has become possible to select those oocytes or eggs with a specific size. In this case, it is preferable to provide a storage medium for storing the membrane potential data of the oocytes or eggs such that the selecting means can select based on the stored information.

For collecting oocytes or eggs with a specific size, it is preferable to use a filter having a definite pore size. Since oocytes have a diameter of about 1.2 mm, the filter pore size is preferably not more than 1.4 mm. The filter may have honeycomb-like pores or round pores. A filter having a plurality of pores with a diameter of 1.0–1.4 mm may be used to sort out oocytes or eggs having a diameter within a certain desired range.

The present invention further provides an apparatus for selecting oocytes or eggs comprising means for selecting oocytes or eggs with a specific size and means for measuring the membrane potentials of the oocytes or eggs. By this, it becomes possible to select oocytes or eggs whose size and membrane potential are within respective specific ranges.

The invention further provides a tray for measuring the membrane potentials of oocytes or eggs which is characterized in that it has a container for receiving an oocyte or egg and that the inside of the container has a metal coating for grounding. The method for selecting oocytes or eggs further comprises a measuring step or steps for selecting oocytes or eggs.

The method according to the present invention comprises the step of measuring the membrane potentials of oocytes or eggs or the step of measuring the sizes of oocytes or eggs, or both the steps. By this method, those oocytes or eggs which have a membrane potential and/or a size each within a certain specific range can be selected.

A filter having a certain specific pore size can be used in the step for measuring the membrane potentials of oocytes or eggs.

The invention further stores the membrane potential information concerning the oocytes or eggs selected and the correlations with cellular responses.

Based on the above-mentioned invention directed to an apparatus or method for selecting oocytes or eggs, the present invention further provides a plurality of oocytes or eggs with a membrane potential and/or a size within a specific ranges.

Thus, the present invention provides a plurality of oocytes or eggs with a specific membrane potential. When considering sample introduction or the like, an appropriate membrane potential is within the range of, for example, −70 to −40 mV. Oocytes or eggs having a membrane potential within this range are expected to provide high levels of protein expression efficiency when a gene, for instance, is introduced into them. According to the invention, the selecting criteria can be expressed numerically, as mentioned above, and it is thus possible to select those oocytes or eggs which meet certain predetermined criteria. Furthermore, by appropriately selecting the criteria, it is possible to decide and select the quality of a cell population in an appropriate manner. It is thus possible to select a cell population meeting an objective quality level, from oocytes or eggs with respect to the survival rates, the fertilization rates, the gene transfer efficiency, the expression efficiency, etc.

In a further aspect of the invention, it is possible to provide a transgenic or like oocyte or egg population by selecting those oocytes or eggs satisfying a certain predetermined criterion, namely, a specific membrane potential, and introducing a sample, such as a gene, into them. For example, an oocyte or egg population selected based on the condition that they have a membrane potential within the range of −70 to −40 mV, followed by gene transfer, is expected to show a high level of protein expression efficiency.

The present invention still further provides a method for selling or transferring a plurality of oocytes or eggs comprising a step of preparing a plurality of oocytes or eggs with a specific membrane potential.

In a further aspect, the invention provides a method for selling or transferring oocytes or eggs comprising a step of attaching the membrane potential information or other quality information to a plurality of oocytes or eggs or to the container via a label carrying that information. The information on the membrane potential includes the membrane potential range for the oocytes or eggs, the measurement conditions, the date of measurement, and so forth.

In a still further aspect, the invention provides a method for selling or transferring a plurality of oocytes or eggs while guaranteeing the quality thereof with respect to the membrane potential.

The present invention thus provides a group of a plurality of oocytes or eggs selected according to objective criteria together with information thereon.

Further, the invention provides a method for producing oocytes which comprises a step of measuring oocytes for the membrane potential, a step of sorting the oocytes based on the membrane potential measurement results to obtain a plurality of oocytes, and a step of injecting a sample into the plurality of oocytes at substantially the same depth.

Other and further objects, features and advantages of the invention will appear more fully from the following description.

BRIEF DESCRIPTION OF THE DRAWINGS

The preferred embodiments of the present invention are illustrated in the accompanying drawings in which.

DETAILED DESCRIPTION OF THE PREFERRED EMBODIMENTS

Figure 1:
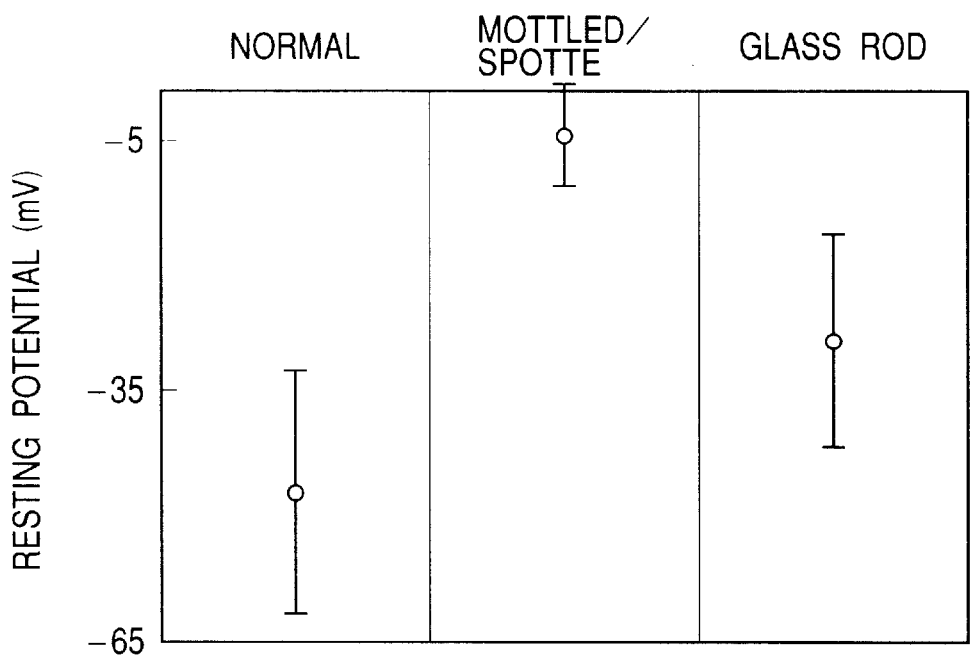
FIG. 1 shows the relationship between the membrane potential and the cell shape.

In the following, the present invention is described in further detail referring to the drawings.

FIG. 1 illustrates one principle of the invention.

Here, Xenopus laevis oocytes are taken as an example. It is to be noted, however, that the invention is not restricted to Xenopus laevis oocytes.

Xenopus laevis oocytes are excised from the female animal's body and treated with an enzyme (e.g. collagenase) for separating them one from another. Thereafter, the oocytes are washed with an appropriate solution, such as ND96 (NaCl 96 mM, KCl 2 mM, $CaCl_2$ 1 mM, $MgCl_2$ 1 mM, HEPES 5 mM(pH7.5)) and then subjected to membrane potential measurement. In the case of Xenopus laevis oocytes, the membrane potential shortly after enzyme treatment (about 2 hours after enzyme treatment) is between 0 to −70 mV. Those oocytes with a membrane potential not less than −10 mV have one or more remarkable spots on the cell surface and/or show an indistinct boundary between the black and while surfaces (FIG. 1). Among those with a membrane potential of −20 mV to −40 mV, there are a fairly large number of oocytes with a substantially spherical shape (FIG. 1). Thus, by measuring the membrane potential, it sorts out oocytes with the desired shape without any visual observation.

Figure 2:
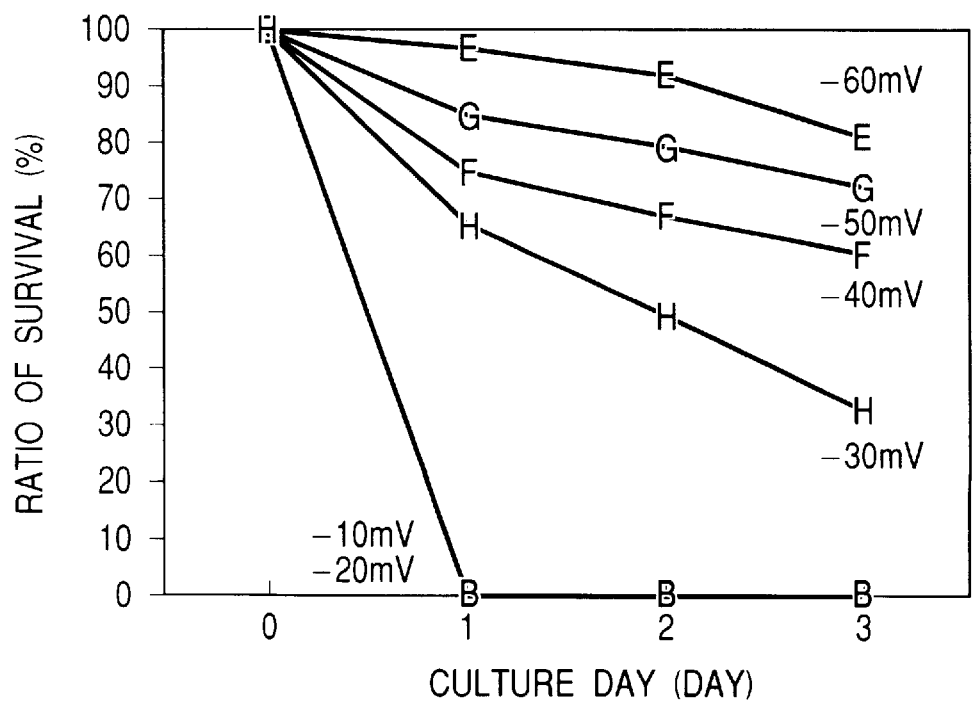
FIG. 2 shows the relationship between the membrane potential and the survival rate.

In the case of Xenopus laevis oocytes, there is a correlation between the membrane potential directly after enzyme treatment and the subsequent cell survival rate, as shown in FIG. 2. The survival rate, at 24 hours after enzyme treatment, of those oocytes showing a membrane potential of not less than −20 mV after enzyme treatment is 0%. Thereafter, until day 4, those deeper in membrane potential after enzyme treatment (larger negative membrane potential, i.e., with larger absolute potential value) show a higher survival rate. Thus, the survival rate of cells is estimated by using the membrane potential directly after enzyme treatment as an index.

An example of injection of a sample into oocytes is now described. The sample to be introduced includes genes, dyes, proteins, peptides, medicinal compounds or the like. In the case of gene injection, the genes may be a cDNA, a cRNA, a DNA, a RNA, synthetic oligonucleotides or the like. This sample injection is carried out with a needle, such as a pipette.

Figure 3:
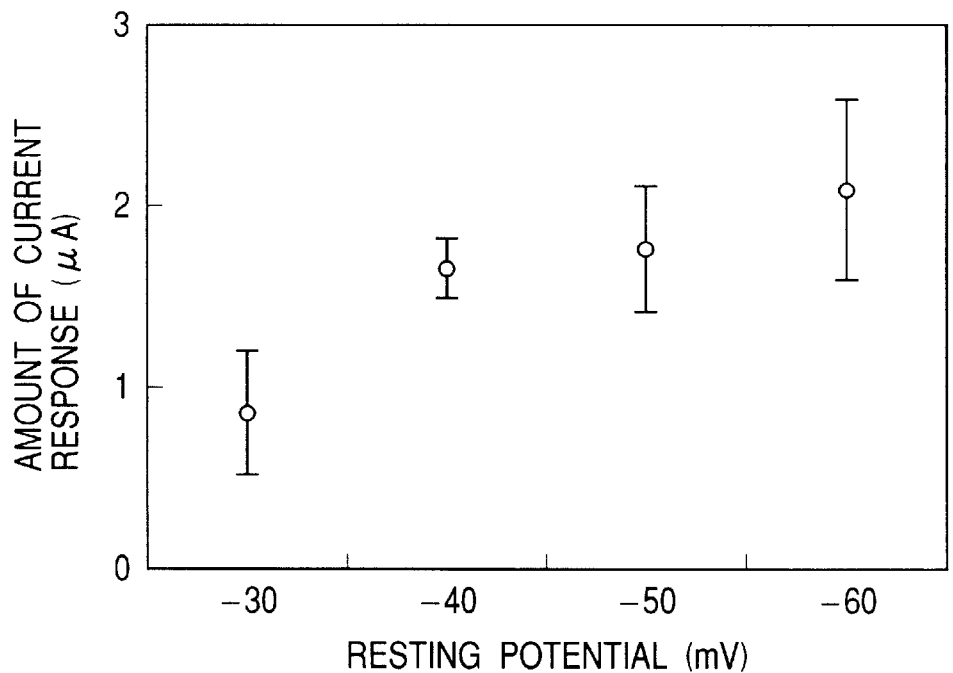
FIG. 3 shows an example of the relationship between the membrane potential and the cellular current response.

In the case of Xenopus laevis oocytes, there is a correlation between the membrane potential directly after enzyme treatment and the protein function expression level after gene transfer, as shown in FIG. 3. Here, the protein function expression level increases as the amount of current response increases. The results shown here are the ones obtained by introducing the histamine receptor gene into Xenopus laevis oocytes and measuring the response to histamine. The use of the histamine receptor gene and the response to histamine in this example do not limit scope of the invention. The cells are stimulated with 1$\mu$M histamine after three days of incubation following introduction of the histamine receptor gene, and the electric response is measured. Those cells with a deeper membrane potential as measured directly after enzyme treatment show a stronger electric response. The invention selects those cells showing a certain specific level of protein function expression by measuring the membrane potential shortly after enzyme treatment. By obtaining a plurality of cells almost equal protein expression level via the invention, it becomes possible to realize a high precision screening for oocytes or eggs to be reacted with different ligands so as to compare the results.

Figure 4:
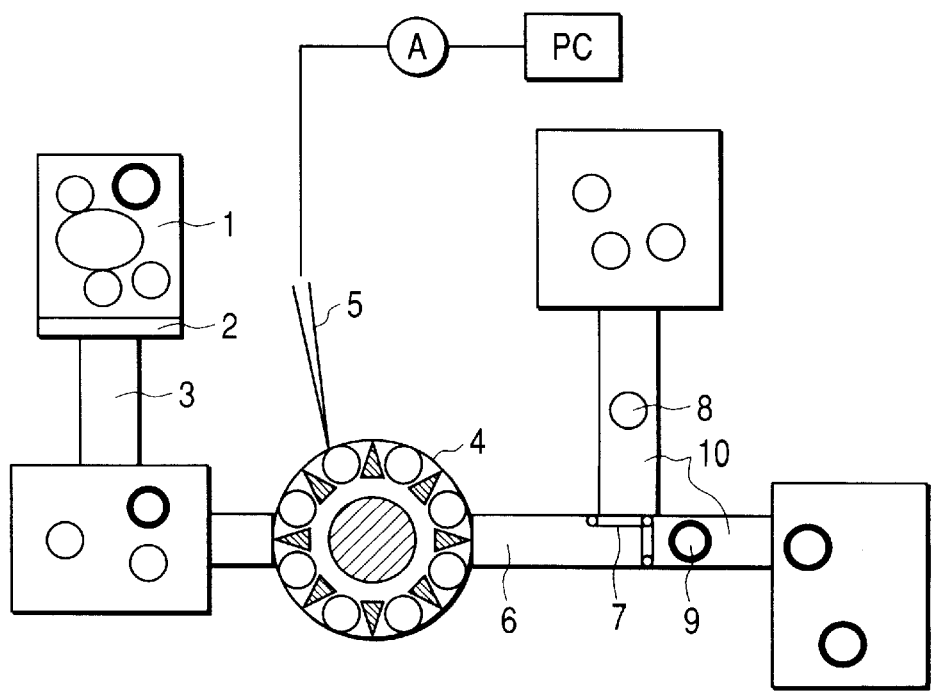
FIG. 4 shows one embodiment of the apparatus of the present invention.

Further, based on this principle, the invention provides an apparatus for selecting oocytes or eggs. Here, an apparatus for selecting Xenopus laevis oocytes is described referring to FIG. 4. Such as apparatus is limited to the selection of Xenopus laevis oocytes, however. The group of Xenopus laevis oocytes includes a number of cells not fully isolated just after enzyme treatment. The group of cells are filtered, for example, through a filter 2 having a honeycomb structure with holes having a diameter of 1 mm and cells having a specific size are thereby selected. Applying an appropriate pressure can speed up the filtering. The cells selected run through a wedge-shaped or semispherical channel 3 having an inclination of 25 to 90 degrees from the horizontal plane and a radius of 1 to 2 mm. This channel is filled with a buffer solution. The buffer solution has a pH of 7.5 and comprises the following compositions.

| | |
|---|---|
| NaCl | 96 mM |
| KCl | 2 mM |
| CaCl$_2$ | 1.8 mM |
| Mg Cl$_2$ | 1 mM |
| HEPES | 5 mM |
| Gentamicin sulfate | 50 $\mu$g/ml |
| Sodium pyruvate | 2.5 mM |
| Penicillin | 10 U/ml |
| Streptomycin | 10 $\mu$g/ml |

Figure 5:
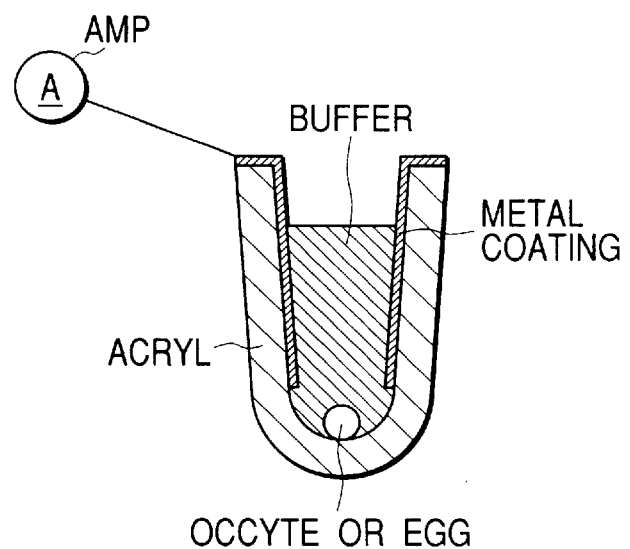
FIG. 5 is a magnified view showing a container having a metal coating on the inside surface and an oocyte or egg placed therein according to the invention.

A gear 4 is provided to retain the oocytes in the middle of a channel to be measured for membrane potential. The inside of the gear 4 is provided with a metal coating for grounding. In this embodiment, the container to be used in membrane potential measurement also functions as a gear. In FIG. 5, there is shown a magnified view of the constitution of a container for receiving one oocyte or egg and having a metal coating on the inside surface thereof.

The rotation of the gear 4 is stopped at each fixed spot for receiving the cell, a cell on the gear is pierced from above in the vertical direction with a glass electrode 5 filled with 3 M KCl, and the membrane potential of the cell is measured. By opening or closing a valve 7 provided in a channel 6 according to a predetermined membrane potential value, a cell 8 satisfying the membrane potential requirement and a cell 9 not satisfying the requirement are separated to respective different channels 10. In this manner, those cells 8 which satisfy the membrane potential requirement are collected in one group.

While, in this example, a glass electrode 5 is used as the means for measuring the membrane potential, the means required for obtaining such information is not limited to such a glass electrode method. For example, the membrane potential of a cell can also be determined based on the information provided by a voltage sensitive dye or a metal electrode.

Figure 6:
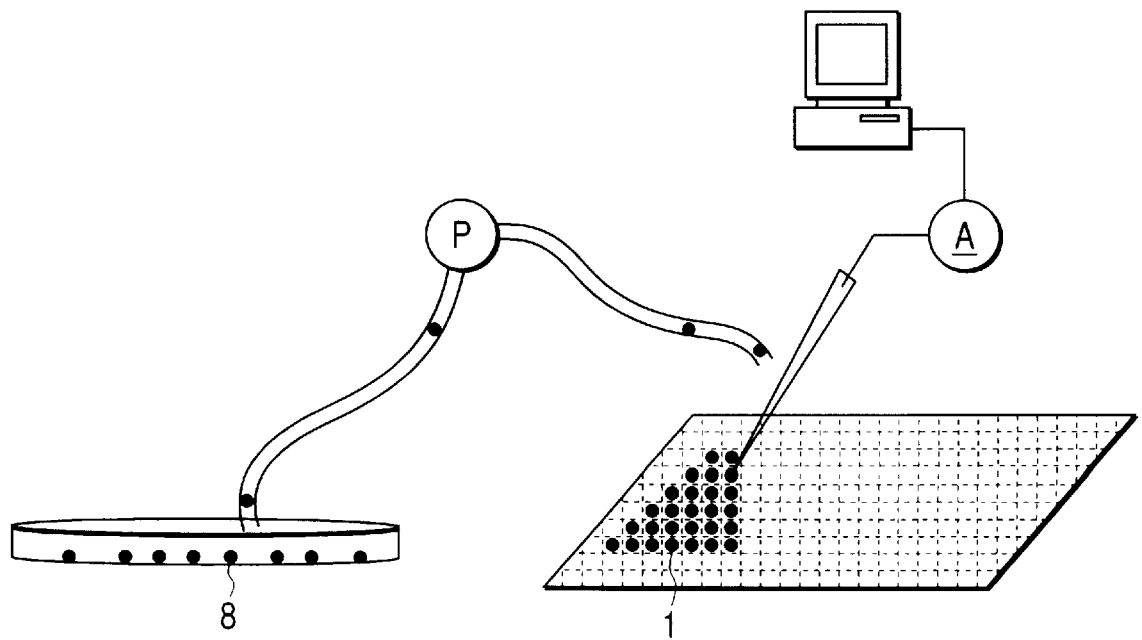
FIG. 6 shows another embodiment of the apparatus of the present invention.

Another embodiment of the apparatus of the present invention is shown in FIG. 6. In this embodiment, each oocyte or egg is put in a respective well in a plate having a plurality of wells, while each well is identified based on the address information. After measuring the membrane potential of the individual oocytes or eggs, the information obtained is stored into a storage medium, such as a CD, LD, DVD, or RD in a computer (control unit), together with the address information regarding the locations of the cells. Later or shortly after the measurement, cells satisfying a predetermined membrane potential criterion are taken out, based on the recorded information with a pump, for instance.

Thus, by using the method and apparatus, the invention can sell or transfer a plurality of oocytes or eggs meeting at least one objective selection criterion. Therefore, the invention provides oocytes or eggs which are guaranteed to be selected according to at least one specific selection criterion.

Further, to the invention collects, sells or transfers only those oocytes or eggs which have a specific membrane potential. On the occasion of sale or transfer, a plurality of oocytes or eggs are packaged and labeled with information concerning the membrane potential conditions.

Figure 7:
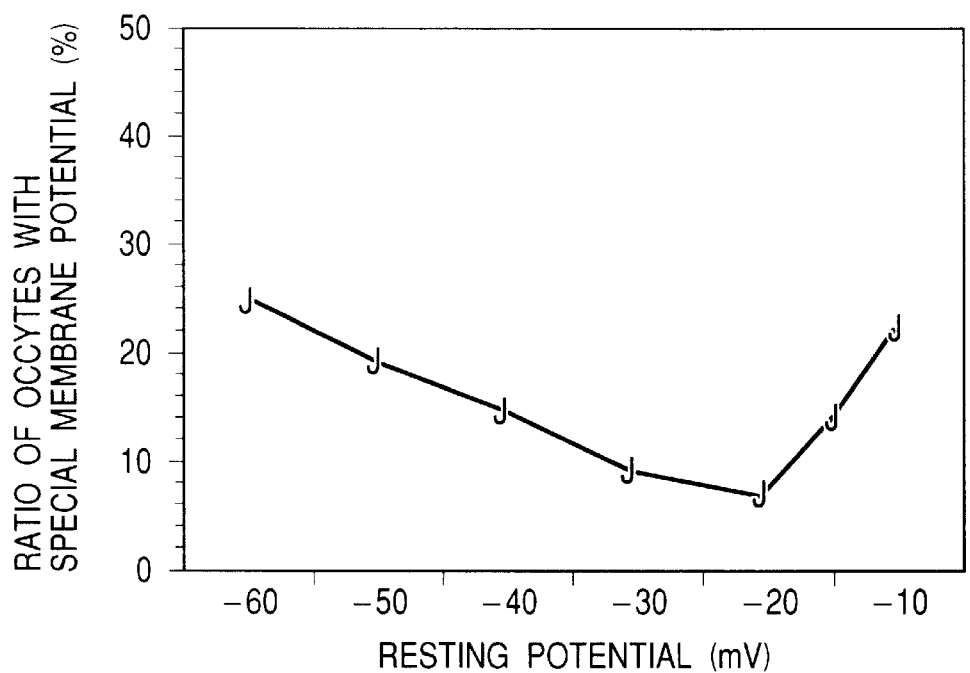
FIG. 7 shows the distribution of oocytes with specific membrane potential in an oocyte population.

FIG. 7 shows the resting potential distribution for a Xenopus laevis oocyte population without undergoing any selection process. While, as mentioned above, Xenopus laevis oocytes shortly after enzyme treatment have a membrane potential within the range of 0 to −70 mV, the proportions of the sub-populations respectively showing membrane potentials of below −55 mV (−60), −55 to −45 mV (−50), −45 to −35 mV (−40), −35 to −25 mV (−30), −25 to −15 mV (−20), and above −15 V are about 26%, 20%, 15%, 10%, 6%, and 22%, respectively. Although this distribution may vary according to the cell species and collection conditions, the proportion in which desired cells to be selected from a cell population is recognizable by using a membrane potential range as a selection criterion. If a higher selection criterion is employed, cells of higher quality are obtained but the number of cells decreases, as showing in FIG. 7, and their sale price inevitably becomes higher. If, conversely, a lower criterion is used, the number of selected cells becomes relatively large, and their price becomes lower although the cells fluctuating in quality.

Figure 8:
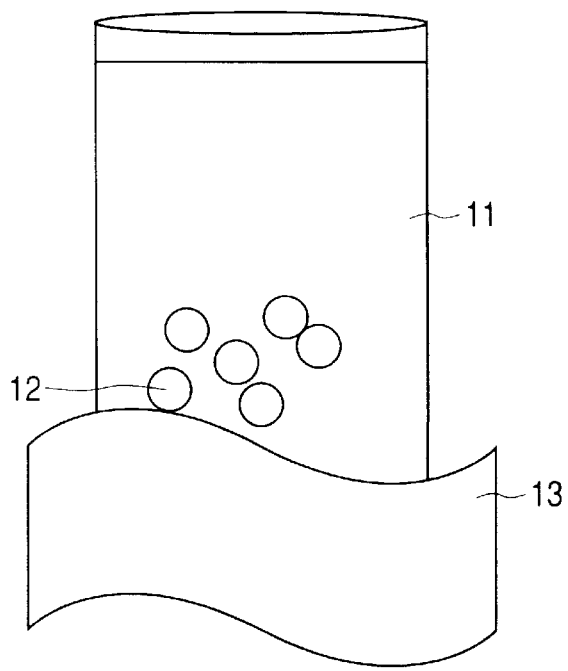
FIG. 8 shows a method of transporting oocytes or eggs.

The method of the invention for transporting oocytes or eggs after membrane potential measurement is now described referring to FIG. 8. In selling and transporting the above oocytes or eggs, the oocytes or eggs 12 are put in a container 11 filled with a solution prepared by adding an antibiotic, such as gentamicin sulfate, penicillin or streptomycin, to a buffer generally used for oocytes or eggs of the relevant organism, and transported using a packaging material 13 made of foamed polystyrene while avoiding collision.

Any of those containers, in which cells can move relatively freely and which have a cap or lid capable of being opened and shut tightly, may be used as the container 11 for selling and transporting the cells. It is desirable that the container be filled with the above-mentioned solution up to about 95% of the capacity thereof. In the case of a conical tube, for instance, 100 to 200 cells, preferably about 130 to 180 cells, are putted in the tube. This cell density corresponds to about 0.3 to 0.5 ml per cell. The cell density can vary according to the cell species, container types, etc.

The above method transports oocytes or eggs to the purchaser's address without impairing any of their functions.

On the occasion of sale or transfer, the membrane potential information for selection is provided. For doing so, a document describing the information may be attached or labeled on the container 11, for instance.

The membrane potential of an oocyte or egg becomes shallower, i.e., smaller negative potential, gradually from directly after isolation with the lapse of time, and the oocyte or egg become more and more unsuitable for the intended use, such as introducing a sample. Specifically, the mean membrane potential value changes thereafter, a number of cells are dead, hence the mean value is calculated with regard to surviving cells alone.

TABLE 1

|  | Mean membrane potential |
| --- | --- |
| Just after treatment (day 0) | −45 mV |
| Day 1 (after 24 hours) | −35 mV |
| Day 2 (after 48 hours) | −25 mV |
| Day 3 (after 72 hours) | −20 mV |
| Day 4 to day 7 | −15 mV |

Since the membrane potential changes with the lapse of time in the above manner, it is recommended that the membrane potential should be measured within 24 hours, preferably within 12 hours, after enzyme treatment.

Therefore, when a gene is to be introduced into Xenopus laevis oocytes, it is desirable that the introduction be finished within 40 hours, in particular within 36 hours, after enzyme treatment.

Figure 9:
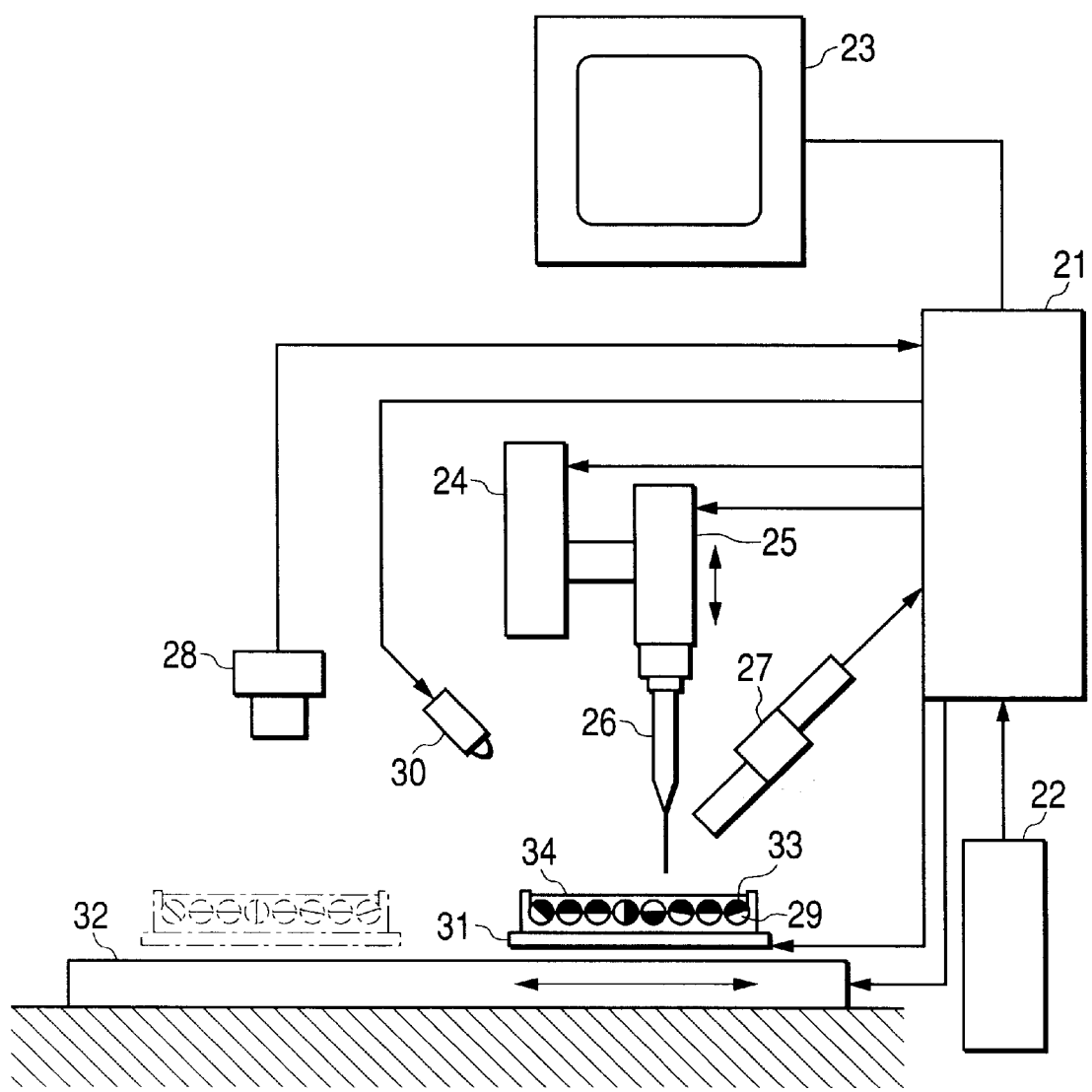
FIG. 9 shows an embodiment of the automatic injection device to be used in the practice of the present invention.

Now, an example of injecting sample. into oocytes (following membrane potential measurement) with an automatic injection device is described referring to FIG. 9.

In the automatic injection device shown in FIG. 9, a tray for disposing oocytes in order has 96 wells uniform in depth and shape (12 in an x direction x 8 in a y direction). The number of wells on the tray is not restricted to 96, however. The wells for disposing oocytes preferably have a cylindrical shape (with a round, flat bottom and with cross sections bottom being always the same from the bottom to the opening) or a conical shape. The diameter of the opening of each of the above wells should be not smaller than the diameter of the oocyte. Further, there should be enough room for the oocyte to rotate in the well. Specifically, the well diameter is about 105 to 150% of the oocyte diameter. Since Xenopus laevis oocytes have a diameter of about 1.3 mm, a well diameter of about 1.4 to 2 mm can immobilize the cells in a particular direction without damaging them.

The needle for introducing a sample, such as a gene, preferably has a pipette-like shape. In this example, a digital camera 28 is used for obtaining cell information concerning the direction of each oocyte. The visual information obtained through a CCD camera 27 is utilized to detect the contact of the introducing needle with the oocyte surface. However, the means for obtaining such information is not limited to a digital camera 28 or a CCD camera 27. For example, the cell surface can be detected based on the information obtained through a sensor fixed on the introducing means for detecting a change in pressure, temperature, electricity, humidity or, pH.

Oocytes after membrane potential measurement but before sample introduction are placed in the wells of the tray 29. The tray 29 is then filled with physiological saline 34, and placed on the stand 31 (for orthogonal movements) over a stand 32 (for horizontal movements). The position of the oocyte 33, into which the sample is to be introduced from the introducing needle 26, is preferably controlled in the directions of X axis and Y axis by means of the same orthogonally moving stand 31 and the same horizontally moving stand 32. In another embodiment of the invention, the tray is fixed, and the introducing needle is mobile.

When the tray 29 is in the position shown by a broken line, the photograph of an oocyte is taken by the digital camera 28. By sending the photographic data to a controller 21, it is possible to store the information concerning the quality of the oocytes and the polarity direction.

By operating the horizontally moving stand 32 and orthogonally moving stand 31 according to the indication of the controller 21, the center of a first oocyte 33 at a predetermined position among the oocytes arranged on the tray 29 is transferred to a position below the gene introducing needle 26. An introducing needle moving arm 24 for moving the introducing needle in the direction of Z axis is operated according to the indication of the controller 21 so as to descend the tip of the introducing needle 26 mounted on an introducer 25 to a position slightly apart from the oocyte surface, for example at a distance of several hundred millimeters. Then, while observing the picture taken by the CCD camera 27 on a monitor 23, the introducing needle moving arm 24 is descended at a low rate by commanding through an auxiliary controller 22. The introducing needle moving arm 24 is stopped upon detecting the contact of the tip of the introducing needle 26 with the surface of the oocyte 33 based on the visual information or the change in pressure, temperature, electricity, humidity, pH, etc. This position serves as a reference point for the subsequent gene transfer operation. The controller 21 stores this position, and the subsequent procedure is carried out. Thus, the distance of vertical movement, or depth, relative to the plane on which the tray is position, of the introducing needle from the above reference point to the site of sample introduction is determined. The oocyte is pierced with the introducing needle 26 at the predetermined depth such that a predetermined amount of the sample is discharged into the cell. For sample introduction, the introducing needle 26 is controlled in the direction of z axis such that it is lowered by 0.2 mm, for instance, below its contact with the surface of the oocyte 33. The depth of the introducing needle 26 appropriate for sample introduction varies according to the sample species and the purpose of introduction. If the depth for introduction is too shallow, the sample will not be distributed sufficiently in the cell. If the depth is excessive, the nucleus or the cell may be damaged. Therefore, from the viewpoint of efficiency, it is desirable that the sample introduction be effected at an almost constant depth. In the case of intracellular introduction of an MRNA for protein expression, for instance, it is desirable that the needle be introduced to a depth of 0.02 to 0.1 mm from the cell surface. On the other hand, in the case of intranuclear introduction of a DNA for protein expression, it is desirable that the needle pierces into the cell at a depth of 0.05 to 0.2 mm from the cell surface. Since the oocyte is slightly deformed upon contacting by the needle, the sample is introduced into the cell actually at a site shallower than the predetermined depth. The time for sample introduction is determined by the period of resting the needle in the cell according to the dose of the sample to be injected into the cell and other factors. For further improving the introduction efficiency, a plurality of introducing needles 26 may also be used. In this case, the driving portion of the apparatus satisfactorily adjusts the position of the introducing needles relative to the tray by unidirectional (one-dimensional) or bi-directional (two-dimensional) movement.

Thereafter, based on the three-dimensional position of the first oocyte, the sample is automatically introduced into the second and an arbitrary number of subsequent oocytes on the tray 29 at an indicated time and rate, and at an indicated introduction depth under automatic control. Alternatively, since the oocytes vary in size, it is also possible to provide a function to detect the surface position on each occasion of sample introduction. It is also possible to store the cell information concerning oocytes in a computer and draw necessary information therefrom when necessary.

Furthermore, the invention stores the movement of the introducing needle 26 and of the oocyte 33 on the occasion of sample introduction, and the visual information concerning the oocyte at the time of sample introduction is stored in the computer such that the site and depth of sample introduction and the characteristics of the cell, for instance, can be read therefrom after completion of the first introduction procedure. In this case, it is desirable that the visual information concerning each oocyte be associated with the site on the tray by numbering.

By using an apparatus having the above constitution, it is possible to rapidly introduce a sample into a large number of oocytes at a specific site and a specific depth so as to produce oocytes of almost equal quality with respect to the efficiency of the sample introduced (introduction efficiency). Thus, the present invention provides a method for introducing a sample into oocytes having a membrane potential in a specified range at a specified site and a specified depth.

Therefore, by using the above automatic injection apparatus, it becomes possible to sell or transfer a plurality of oocytes having a membrane potential in a predetermined range and to attain an introduction efficiency of about 80 to 90% under controlled sample introduction conditions.

Therefore, the present invention provides amphibian oocytes having a membrane potential within a certain specified range, and assures sample introduction thereinto at a specified site and at a specified depth.

When sample introduction is performed using such an automatic injection device, the sample can be injected into oocytes having a membrane potential within a specific predetermined range under substantially the same conditions. Therefore, an oocyte population almost uniform in protein expression level, for instance, can be obtained. Since this is an almost homogeneous oocyte population, it is particularly useful for screening purposes.

The present invention obtains oocytes or eggs meeting at least one objective selection criterion. By storing the cell selection criteria information, it becomes possible to obtain a correlation thereof with the survival rate, fertilization rate, gene transfer efficiency or the like.

It is also possible to collect, sell, or transfer only those oocytes or eggs which have a specific membrane potential.

The foregoing invention has been described in terms of preferred embodiments. However, those skilled in the art will recognize that many variations of such embodiments exist. Such variations are intended to be within the scope of the present invention and the appended claims.

What is claimed is:

1. A selection apparatus for selecting oocytes or eggs comprises measuring means for measuring a membrane potential of each of the oocytes or eggs and selecting means for selecting the oocytes or eggs based on the membrane potential measurement results.

2. The selection apparatus as claimed in claim 1 further comprise a storage medium for storing the measured membrane potentials such that the selecting means selects based on the stored information.

3. The selection apparatus as claimed in claim 1, wherein the measuring means includes a container for receiving an oocyte or egg and the inside of the container has a metal coating for grounding thereby measuring the membrane potential therein.

4. The selection apparatus as claimed in claim 1 further comprises collecting means for selectively collecting oocytes or eggs selected by the selecting means.

5. The selection apparatus as claimed in claim 1, further comprises size measuring means for measuring a size of each of the oocytes or eggs thereby sorting out the oocytes or eggs based on the size measurement results.

6. The selection apparatus as claimed in claim 5, wherein the size measuring means is a filter.

* * * * *